United States Patent
Yue et al.

(10) Patent No.: US 10,858,337 B2
(45) Date of Patent: Dec. 8, 2020

(54) METHOD FOR PREPARING 1,1'-ETHYLENE-2,2'-BIPYRIDINIUM DICHLORIDE

(71) Applicant: NANJING REDSUN BIOCHEMISTRY CO., LTD., Jiangsu (CN)

(72) Inventors: Ruikuan Yue, Nanjing (CN); Yi Xue, Nanjing (CN); Honglong Chen, Nanjing (CN); Wenkui Wang, Nanjing (CN); Chaoran Luo, Nanjing (CN); Xinchun Chen, Nanjing (CN); Dianhai Zhou, Nanjing (CN); Jianhua Jiang, Nanjing (CN); Fujun Wang, Nanjing (CN)

(73) Assignee: NANJING REDSUN BIOCHEMISTRY CO., LTD., Nanjing (CN)

( * ) Notice: Subject to any disclaimer, the term of this patent is extended or adjusted under 35 U.S.C. 154(b) by 0 days.

(21) Appl. No.: 16/650,115

(22) PCT Filed: Oct. 13, 2017

(86) PCT No.: PCT/CN2017/106013
§ 371 (c)(1),
(2) Date: Mar. 24, 2020

(87) PCT Pub. No.: WO2019/041462
PCT Pub. Date: Mar. 7, 2019

(65) Prior Publication Data
US 2020/0308138 A1   Oct. 1, 2020

(30) Foreign Application Priority Data
Aug. 30, 2017 (CN) .......................... 2017 1 0760340

(51) Int. Cl.
*C07D 401/04*   (2006.01)
(52) U.S. Cl.
CPC ................... *C07D 401/04* (2013.01)

(58) Field of Classification Search
CPC ................................................... C07D 401/04
See application file for complete search history.

(56) References Cited

U.S. PATENT DOCUMENTS

| 2,820,065 A | 1/1958 | Slagh |
| 2,823,987 A | 2/1958 | Fielden et al. |
| 3,308,124 A | 3/1967 | Braunholtz et al. |
| 3,674,788 A | 7/1972 | Thomas et al. |
| 3,803,147 A | 4/1974 | Cairns |

FOREIGN PATENT DOCUMENTS

| CN | 106220629 A | 12/2016 |
| CN | 106279166 A | 1/2017 |
| GB | 815348 A | 6/1959 |

OTHER PUBLICATIONS

Homer et al., "Mode of Action of Dipyridyl Quaternary Salts as Herbicides," J. Sci. Food. Agric., Jun. 11, 1960, pp. 309-315.
Daniel et al., "Absorption and Excretion of Diquat and Paraquat in Rats," Brit. J. industr. Med., 1966, vol. 23, pp. 133-136.
Arrieta et al., "Reagents and Synthetic Methods 38. 4-(Dimethylamino)pyridinium Bromide Perbromide as a New Brominating Agent for Organic Compounds," Synthetic Communications: An International Journal for Rapid Communication of Synthetic Organic Chemistry, 1984, vol. 14, No. 10, pp. 939-945.
Naik et al., "A new Recyclable Ditribromide Reagent for Efficient Bromination under Solvent Free Condition," J. Org. Chem., 2005, vol. 70, pp. 4267-4271.
Paul et al., "Hexamethonium bis(tribromide) (HMBTB) a recyclable and high bromine containing reagent," Tetrahedron Letters, 2015, vol. 54, No. 41, pp. 5646-5650.
Akhavein et al., "The dipyridylium herbicides, paraquat and diquat," Residue Reviews, F.A. Gunther (ed.), 1968, pp. 97-145.
May 25, 2018 International Search Report issued in International Patent Application No. PCT/CN2017/106013.

*Primary Examiner* — Timothy R Rozof
(74) *Attorney, Agent, or Firm* — Oliff PLC

(57) ABSTRACT

A method for preparing 1,1'-ethylene-2,2'-bipyridinium dichloride includes mixing an aqueous diquat dibromide solution with hydrochloric acid, adding dropwise to a mixture of an organic solvent, a bromine absorbent, and an oxidant, and reacting to produce 1,1'-ethylene-2,2'-bipyridinium dichloride.

9 Claims, No Drawings

METHOD FOR PREPARING 1,1'-ETHYLENE-2,2'-BIPYRIDINIUM DICHLORIDE

BACKGROUND

Technical Field

The present invention relates to the field of chemistry, and particularly to a method for preparing 1,1'-ethylene-2,2'-bipyridinium dichloride.

Related Art 1,1'-ethylene-2,2'-bipyridinium cationic salt is an excellent contact desiccant and herbicide with systemic properties. 1,1'-ethylene-2,2'-bipyridinium dibromide (Diquat dibromide, CAS number: 85-00-7) is a common 1,1'-ethylene-2,2'-bipyridinium cationic salt. 1,1'-ethylene-2,2'-bipyridinium dibromide was first developed by Imperial Chemical Industries (ICI), the predecessor of Syngenta, through a preparation method mainly, comprising a cyclization reaction of 2,2'-bipyridine with dibromoethane (U.S. Pat. No. 2,823,987). The cationic moiety is named. Diquat, and it is pointed out that the change of the anion corresponding to Diquat does not destroy its herbicidal activity.

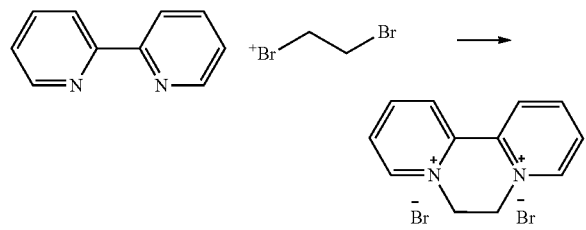

The Patent GB815348 reveals that the change of the anion corresponding to Diquat does not destroy its herbicidal activity. Relevant literature also mentions that the active moiety in herbicides such as paraquat and diquat is the cationic moiety, and relevant anions have no impact on their herbicidal activity (The dipyridylimn herbicides, paraquat and diquat, P99). In these compounds, the anions have no impact on their activity, and Cl⁻, Br⁻, I⁻, $CH_3SO_4^{2-}$, and $SO_4^{2-}$ cause an equal impact to the equimolar amount of substrate (J. Sci. Food Agric., 11 Jun. 1960, 309-315).

Bromine is a precious resource. As is known to all, the traditional method of recovering bromine is to enrich and recover bromine by a series of technological means such as concentration and oxidation of underground brine or seawater, and then it is used to produce important chemical products. Diquat dibromide as a herbicide or desiccant will bring bromine into the environment during use, causing unnecessary waste.

As a relatively cheap resource, chlorine is suitable for use as a counter ion for diquat cation. There is no suitable industrialized preparation method for diquat dichloride (1,1'-ethylene-2,2'-bipyridinium dichloride) in the prior art. The existing preparation methods for diquat dichloride are all exploratory. As can be seen from the literatures of ICI Company, the following several attempts are made:

1. Ion exchange method. It is mentioned in the U.S. Pat. No. 2,823,987 (Example 4) that a diquat dichloride solution is obtained by reacting a diquat dibromide solution with silver chloride with fully stirring, and then filtering off the silver bromide.

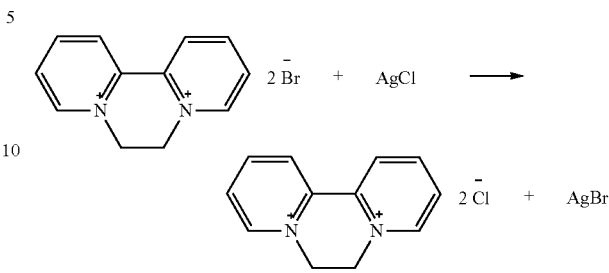

It is also reported (Brit. J. industr. Med., 1966, 23, 133) that an ion exchange resin can be used to obtain diquat dichloride through ion exchange.

2. The U.S. Pat. No. 3,308,124 provides a new method for the preparation of diquat dichloride (or dibromide), which comprises specifically introducing ethylene and chlorine of an equimolar amount to a mixed solution of 2,2'-bipyridine, a catalyst (such as NaCl, glass fiber, and silica gel), and a solvent (such as nitrobenzene). However, it is pointed out that diquat dichloride cannot be produced with dichloroethane and 2,2'-bipyridine under these conditions, and the conversion rate of raw materials and the product yield are not mentioned.

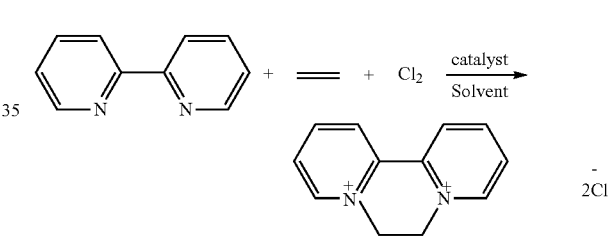

3. U.S. Pat. No. 3,803,147 reveals a method for preparing diquat dichloride (Example 11), which comprises coupling ethylene-bis-pyridinium bromide with sodium amalgam in a solvent, and then oxidizing the resulting 1,1'-ethylene-1,1'-dihydro-2,2'-bipyridinium dibromide in dilute hydrochloric acid in the air atmosphere, to obtain diquat dichloride.

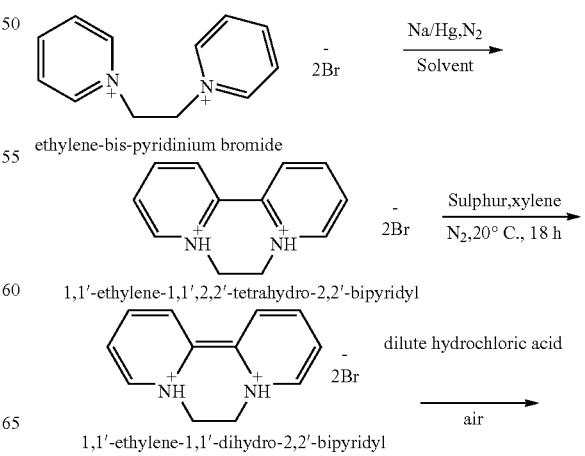

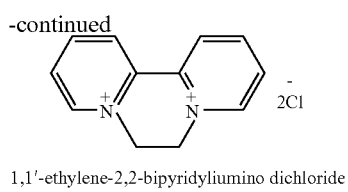

1,1'-ethylene-2,2-bipyridyliumino dichloride

In CN201610605417 filed by the applicant, chlorine is used for ion exchange in CN201610605417 to prepare diquat dichloride, and then bromine is distilled off at a high temperature. This method has certain difficulties and limitations. One reason is that diquat dibromide or diquat dichloride can be bound with bromine to produce an adduct of Formula II, specifically as shown in Formulas III and IV. The adduct obtained by this method is a mixture of III and IV. Since the adduct is insoluble in water, it will be precipitated out from the reaction system. The diquat dichloride compound cannot be obtained.

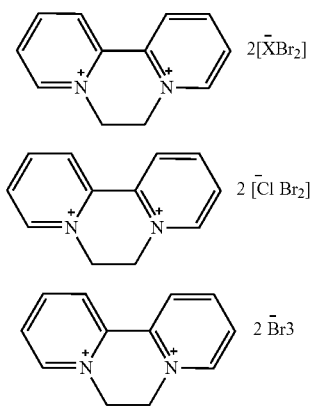

The Great Lakes Chemical Corporation, USA, also studied the adduct of Formula II in U.S. Pat. No. 3,674,788.
The preparation method is as follows:

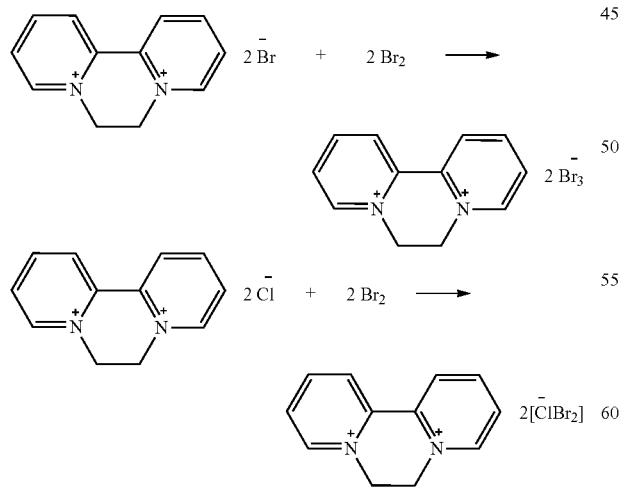

Diquat dichloride does not form an adduct with chlorine. Chlorine is introduced into an aqueous diquat dibromide solution, by which the bromide is oxidized to bromine element. Bromine element can form an adduct with diquat dibromide or diquat dichloride.

In addition, the applicant found through experiments that the bound bromine can be dissociated from the adduct of Formula II in water by heating, and the bromine element is distilled off. However, during the dissociation process, bromine is reacted with water to generate hypobromous acid (HBrO). The bipyridinium salt is oxidized by hypobromous acid, causing loss of more diquat cations. This is unacceptable in industrial production.

As is well known, the bipyridinium (bromide) be further reacted with bromine to form a tribromide. This tribromide, such as the common pyridinium tribromide (Formula V), can be used as a brominating agent in the addition reaction of double bonds and the substitution reaction with phenols, and good reaction characteristics are exhibited. Studies on brominating agents such as $DMAP.HBr_3$ (Formula VI) (SYNTHETIC COMMUNICATIONS, 1984, 14 (10), 939-945), 1,2-Dipyridiniumditribromide-ethane (DPTBE) (Formula VH) (J. Org. Chem. 2005, 70, 4267-4271), 1,10-(ethane-1,2-diyl)phenanthrolinediniumbistribromide (EPDBT) (Formula W) (Tetrahedron Letters, 2015, 56(41), 5646-5650) and others are also described. In the related reactions involving these brominating agents, good results are obtained in terms of the selectivity and yield.

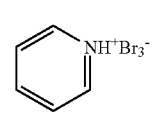

Pyridinium tribromide

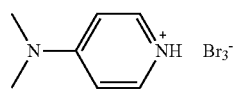

4-Dimethylamino-pyridinium tribromide

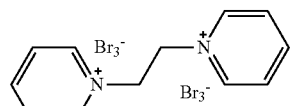

1,2-Dipyridiniumditribromide-ethane (DPTBE)

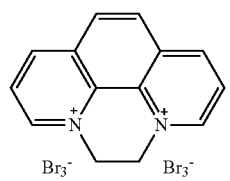

(1,10-(ethane-1,2-diyl)phenanthrolinediium bistribromide (EPDBT)

Therefore, there is an urgent need in the art for a method that can be used to smoothly produce diquat dichloride, and reasonably convert the produced bromine into other more important compounds.

SUMMARY

In view of the problems existing in the preparation technology of diquat dichloride in the prior art, the present invention provides a method torr preparing diquat dichloride (that is, 1,1'-ethylene-2,2'-bipyridinium dichloride), in which an important chemical intermediate bromide is produced as a by-product.

The objects of the present invention can be accomplished through the following technical solutions:

A method for preparing 1,1'-ethylene-2,2'-bipyridinium dichloride is provided, in which an aqueous solution of 1,1'-ethylene-2,2'-bipyridinium dibromide is used as a raw material, and after oxidation with an oxidant, absorption of bromine, liquid separation and other post-treatments, a mother liquor of 1,1'-ethylene-2,2'-bipyridinium dichloride with a cation content of 20-30% and a bromide by-product are obtained.

The method for preparing 1,1'-ethylene-2,2'-bipyridinium dichloride according to the present invention comprises mixing an aqueous diquat dibromide solution with hydrochloric acid, dripping to a mixture of an organic solvent, a bromine absorbent, and an oxidant, and reacting at a temperature of 20-100° C. where the oxidant is hydrogen peroxide. After the reaction, depending on the solubility of the bromide by-product in the reaction system, the following two treatments can be performed. The reaction solution is cooled to 5-30° C., and filtered according to whether a solid is precipitated in the reaction solution.

If a solid is precipitated in the reaction solution, the reaction solution is filtered and separated to obtain an aqueous phase and an organic phase after reaction, the aqueous phase is adjusted to pH 3-7, and concentrated to obtain a mother liquor containing 1,1'-ethylene-2,2'-bipyridinium dichloride. The solid is a crude bromide product, which is washed and dried to obtain a pure bromide product. The washing solvent used is a mixed solvent of organic solvent used in the reaction system and water, where the volume ratio of the organic solvent to water is 5-8:2-5.

If no solid is precipitated in the reaction solution, the reaction solution is directly, separated to obtain an aqueous phase and an organic phase after reaction; an organic solvent is added to the aqueous phase to further extract the remaining bromide in the aqueous phase, to obtain an extracted aqueous phase and an extracted organic phase; the extracted aqueous phase is adjusted to pH 3-7, and concentrated to obtain a mother liquor containing 1,1'-ethylene-2,2'-bipyridinium dichloride; and the organic phase after reaction and the extracted organic phase are combined, concentrated, and crystallized to obtain a crude bromide product, which is then post-treated to obtain a pure bromide product. The post-treatment for the crude bromide product is a conventional separation or purification method well known to those skilled in the art, and specifically includes: one or a combination of more than one of decolorization with activated carbon, recrystallization, and solid granulation or slicing to obtain a pure bromide product.

Ammonium bicarbonate, sodium bicarbonate, or ammonia is used to adjust the aqueous phase or extracted aqueous phase to pH 3-7.

The chemical reaction in the preparation method of diquat dichloride according to the present invention is shown below:

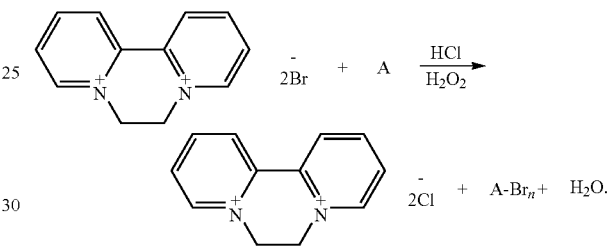

The chemical reaction in the present invention includes: a full reaction of a mixed solution of diquat dibromide and hydrochloric acid with an oxidant, and a reaction of the generated adduct with a bromine absorbent, i.e. the generation of the adduct, and the bromination reaction of the adduct, specifically as shown below:

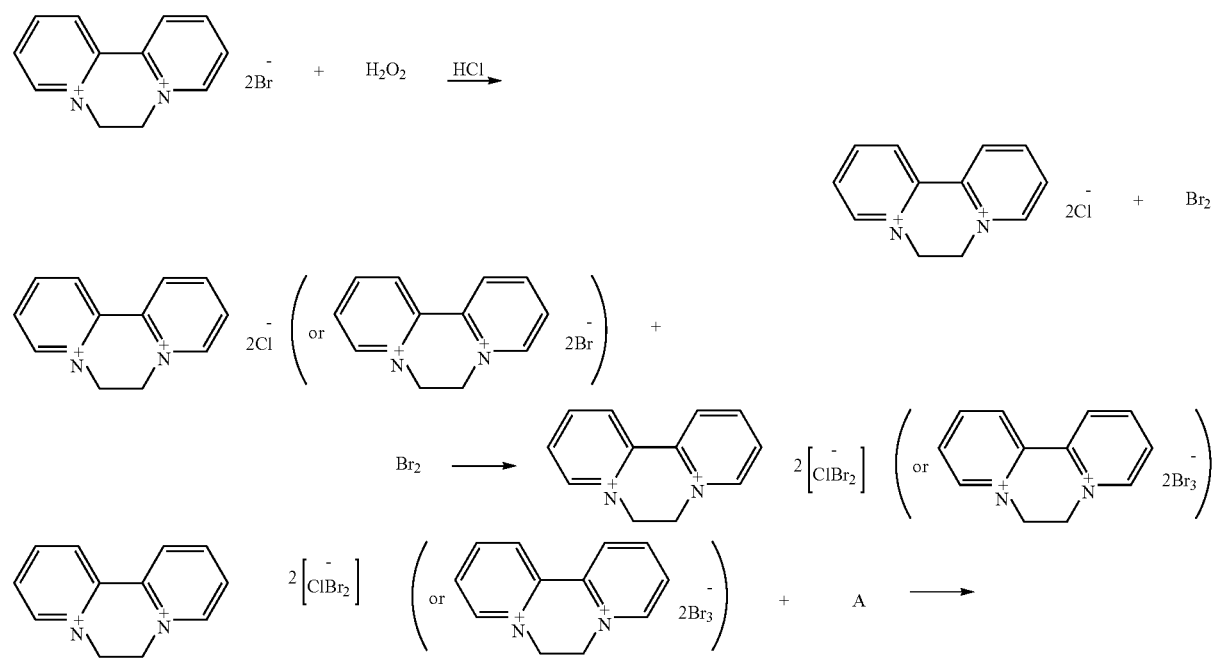

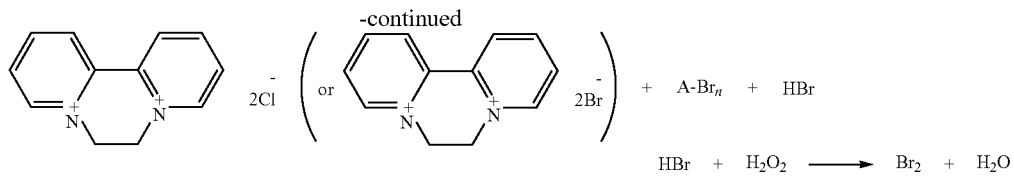

where A is the bromine absorbent, and A-Br$_n$ is the bromide.

The molar ratio of diquat dibromide to hydrochloric acid is 1:2-2.5, and preferably 1:2.2.2. The content in percentage by weight of hydrochloric acidic 30-36%.

The molar ratio of diquat dibromide to the oxidant is 1:2-3. The content in percentage by weight of hydrogen peroxide is 20-50%. If the amount of the oxidant is too low, the bromide ion cannot be completely converted. If the amount is too high, not only the waste of hydrogen peroxide and increase of cost are caused, and also the remaining hydrogen peroxide will be decomposed, so that expansion of the mother liquor of 1,1'-ethylene-2,2'-bipyridinium dichloride may occur during the storage and transportation, causing a potential safety hazard.

The bromine absorbent is phenol, aniline, bisphenol A, bisphenol S, p-cyanophenol, 4-hydroxybiphenyl, ethyl propionate, toluene, thiophene, and p-hydroxybenzaldehyde.

The molar amount of the bromine absorbent is 1-1 times the theoretical molar amount of the bromine absorbent. The theoretical molar amount of the bromine absorbent refers to the molar amount of the bromine absorbent to react with bromine produced by oxidation of per unit molar amount of diquat dibromide. Taking phenol as an example of the bromine absorbent, 1 mol of diquat dibromide theoretically needs ⅔ mol of phenol; and the actual amount of phenol to react with bromine produced by 1 mol of diquat dibromide is 1-1.2 times of ⅔ mol.

The organic solvent in the reaction system is benzene, chlorobenzene, dichloroethane, dibromoethane, cyclohexane, n-heptane, and a $C_3$-$C_7$ monohydric alcohol. The organic solvent used to extract the aqueous phase is the same organic solvent as that in the reaction system, and is used in an amount of 3/10-7/10 of the amount of the organic solvent in the reaction system. The $C_3$-$C_7$ monohydric alcohol mentioned in the present invention is selected from the group consisting of n-butanol, n-propanol, isopropanol, isobutanol, sec-butanol, n-pentanoi, sec-pentanol, 3-pentanol, isopentanol, n-hexanol 1-hexanol, 3-hexanol, 2-ethylbutanol and the like, and preferably n-butanol.

The reaction temperature during the dripping process is controlled at 20-60° C., and the dripping rate based on diquat dibromide is 1.5-3.0 g/min; after the dripping is completed, the temperature is raised to 70-100° C. and the reaction is continued for 1-2 hrs.

The reaction temperature is preferably 50-100° C. The reaction temperature during the dripping process is controlled at 50-60° C., and the dripping rate based on diquat dibromide is 1.5-3.0 g/min; after the dripping is completed, the temperature is raised to 70-100° C. and the reaction is continued for 1-2 hrs.

The cation content in the mother liquor containing 1,1'-ethylene-2,2'-bipyridinium dichloride is 20-30%.

During the dripping process in the present invention, if the reaction temperature is too low, the reaction speed is slow; and if the reaction temperature is high, the decomposition rate of hydrogen peroxide is accelerated, and the loss is serious. Therefore, the reaction temperature is generally controlled to 20-60° C. and preferably 50-60° C. during the dripping process. After the dripping process, the concentration of the raw material is law, so the temperature is raised to 70-100° C. to increase the reaction rate and accelerate the progress of the bromination reaction, and to ensure that the excess hydrogen peroxide in the reaction system is decomposed as much as possible to reduce the occurrence of expansion during subsequent storage and transportation. The applicant has verified through experiments that in the reaction system of the present invention, hydrogen peroxide cannot change the diquat cation. In the method of the present invention, the diquat cations is prevented from being destroyed, and an organic solvent is added to the reaction system to dissolve the bromine absorbent and the bromide after the bromination reaction, thus avoiding the precipitation of the generated bromine in the form of an adduct from the system to affect the progress of the reaction. The entire reaction process occurs in a liquid state, which greatly improves the convenience of operation.

The "%" in the present invention is percentages by weight.

The present invention has the following beneficial effects.

The technical solution of the present invention has the advantages of simple synthesis method that is suitable for industrial production, high yield of diquat dichloride of 98% or more, production of bromide by-product that can be sold in the market, and bromine recovery rate of 96% or more, which reduce the cost and avoids the waste of valuable bromine resources.

DETAILED DESCRIPTION

The present invention will be described in further detail with reference to specific examples. However, the protection scope of the present invention is not limited thereto.

Example 1

An aqueous diquat dibromide solution (150.5 g, 0.5%) was mixed with hydrochloric acid (36.3 g, 36%), and dripped to a mixture of hydrogen peroxide (30.3 g, 46%), n-butanol (150.1 g), and phenol (11.2 g), The temperature of the system was maintained at 60° C., and the dripping rate was controlled such that the dripping process was completed in about 40 min. The reaction solution was heated to 70-80° C., stirred fully to well mix the biphasic liquid, and reacted for 1.5 hrs. After the reaction was completed, the reaction solution was separated to obtain an aqueous phase and an organic phase after reaction. The aqueous phase was extracted with n-butanol (100 g), and separated to obtain an extracted aqueous phase and an extracted organic phase. The extracted aqueous phase was added with ammonium bicarbonate (0.5 g), fully stirred, adjusted to pH 3.5, and concentrated by evaporating off a part of water to give 108.9 g of a mother liquor containing 40.9% diquat dichloride (cation content 29.5%). The yield was 98.5%.

The organic phase after reaction and the extracted organic phase were combined, concentrated, and crystallized to obtain a crude tribromophenol product. The crude product was dissolved in anhydrous ethanol at 70° C., decolored by adding activated carbon, and filtered. The filtrate was mixed with water of equal volume, and recrystallized to obtain a pure tribromophenol product (38.4 g, purity by GC: 99.5%, bromine recovery rate 97.7%).

Example 2

An aqueous diquat dibromide solution (150.2 g, 40.5%) was mixed with hydrochloric acid (35.9 g, 36%), and dripped to a mixture of hydrogen peroxide (30.3 g, 46%), phenyl chloride (250.1 g), and phenol (11.2 g). The temperature of the system was maintained at 60° C., and the dripping rate was controlled such that the dripping process was completed in about 40 min. The reaction solution was heated to 70-80° C., stirred frilly to well mix the biphasic liquid, and reacted for 1.5 hrs. After the reaction was completed, the reaction solution was separated to obtain an aqueous phase and an organic phase after reaction. The aqueous phase was extracted with phenyl chloride (100 g), and separated to obtain an extracted aqueous phase and an extracted organic phase. The extracted aqueous phase was added with ammonium bicarbonate (0.8 g), fully stirred, adjusted to pH 4.0, and concentrated by evaporating off a part of water to give 107.5 g of a mother liquor containing 41.7% diquat dichloride (cation content 30.1%). The yield was 99.4%.

The organic phase after reaction and the extracted organic phase were combined, concentrated, and crystallized to obtain a crude tribromophenol product. The crude product was dissolved in ethanol at 70° C., decolored by adding activated carbon, and filtered. The filtrate was mixed with water of equal volume, and recrystallized to obtain a pure tribromophenol product (38.8 g, purity by GC: 99.6%, bromine recovery rate 99.0%).

Example 3

An aqueous diquat dibromide solution (150.2 g, 40.5%) was mixed with hydrochloric acid (37.2 g, 36%), and dripped to a mixture of hydrogen peroxide (29.3 g, 46%), dichloroethane (300.1 g), and bisphenol A (20.2 g). The temperature of the system was maintained at 60° C., and the dripping rate was controlled such that the dripping process was completed in about 40 min. The reaction solution was heated to 70-80° C., stirred fully to well mix the biphasic liquid, and reacted for 1.5 hrs. After the reaction was completed, the reaction solution was separated to obtain an aqueous phase and an organic phase after reaction. The aqueous phase was extracted with dichloroethane (100 g), and separated to obtain an extracted aqueous phase and an extracted organic phase. The extracted aqueous phase was added with ammonium bicarbonate (1.2 g), frilly stirred, adjusted to pH 4.1, and concentrated by evaporating off a part of water to give 107.3 g of a mother liquor containing 41.9% diquat dichloride (cation content 302%). The yield was 99.7%.

The organic phase after reaction and the extracted organic phase were combined, concentrated, and crystallized to obtain a crude tetrabromobisphenol A product. The crude product was decolored by adding activated carbon, and purified by recrystallization in 95% ethanol to obtain a pure tetrabromobisphenol A product (47.8 g, purity by GC: 99.6%, bromine recovery rate 98.9%).

Example 4

An aqueous diquat dibromide solution 150.2 g, 40.5%) was mixed with hydrochloric acid (38.5 g, 36%), and dripped to a mixture of hydrogen peroxide (29.3 g, 46%), n-butanol (200.4 g) and bisphenol A (20.2 g). The temperature of the system was maintained at 60° C., and the dripping rate was controlled such that the dripping process was completed in about 40 min. The reaction solution was heated to 70-80° C., stirred fully, and reacted for 1.5 hrs. After the reaction was completed, the reaction solution was separated to obtain an aqueous phase and an organic phase after reaction. The aqueous phase was extracted with n-butanol (100 g), and separated to obtain an extracted aqueous phase and an extracted organic phase. The extracted aqueous phase was added with ammonium bicarbonate (2.5 g), fully stirred, adjusted to pH 3.9, and concentrated by evaporating off a part of water to give 107.8 g of a mother liquor containing 41.6% diquat dichloride (cation content 30.0%). The yield was 99.4%.

The organic phase after reaction and the extracted organic phase were combined, concentrated, and crystallized to obtain a crude tetrabromobisphenol A product. The crude product was decolored by adding activated carbon, and purified by recrystallization in 95% ethanol to obtain a pure tetrabromobisphenol A product (41.1 g, purity by GC: 99.5%, bromine recovery rate 98.7%).

Example 5

An aqueous diquat dibromide solution (150.2 g, 40.5%) was mixed with hydrochloric acid (39.2 g, 36%), and dripped to a mixture of hydrogen peroxide (38.5 g, 46%), n-heptane (300.1 g), and phenol (11.2 g). The temperature of the system was maintained at 60° C., and the dripping rate was controlled such that the dripping process was completed in about 40 min. The reaction solution was heated to 70-80° C., stirred fully to well mix the biphasic liquid, and reacted for 1.5 hrs. After the reaction was completed, the reaction solution was separated to obtain an aqueous phase and an organic phase after reaction. The aqueous phase was extracted with n-heptane (100 g), and separated to obtain an extracted aqueous phase and an extracted organic phase. The extracted aqueous phase was added with ammonium bicarbonate (2.5 g), fully stirred, adjusted to pH 3.8, and concentrated by evaporating off a part of water to give 106.7 g of a mother liquor containing 41.9% diquat dichloride (cation content 30.2%). The yield was 99.2%.

The organic phase after reaction and the extracted organic phase were combined, concentrated, and crystallized to obtain a crude tribromophenol product. The crude product was dissolved in anhydrous ethanol at 70° C., decolored by adding activated carbon, and filtered. The filtrate was mixed with water of equal volume, and recrystallized to obtain a pure tribromophenol product (38.8 g, purity by GC: 99.5%, bromine recovery rate 98.8%).

Example 6

An aqueous diquat dibromide solution (150.3 g, 40.5%) was mixed with hydrochloric acid (39.1 g, 36%), and dripped to a mixture of hydrogen peroxide (30.2 g, 46%), cyclohexane (300.5 g), and phenol (11.2 g). The temperature of the system was maintained at 60° C., and the dripping rate was controlled such that the dripping process was completed in about 40 min. The reaction solution was heated to 70-80° C., stirred fully, and reacted for 1.5 hrs. After the reaction was completed, the reaction solution was separated to obtain an aqueous phase and an organic phase after reaction. The aqueous phase was extracted with cyclohexane (100 g), and separated to obtain an extracted aqueous phase and an extracted organic phase. The extracted aqueous phase was adjusted to pH 3.8 with sodium bicarbonate (2.6 g), and concentrated by evaporating off a part of water to give 105.8 g of a mother liquor containing 42.0% diquat dichloride (cation content 30.3%). The yield was 98.5%.

The organic phase after reaction and the extracted organic phase were combined, concentrated, and crystallized to obtain a crude tribromophenol product. The crude product was dissolved in ethanol at 70° C., decolored by adding activated carbon, and filtered. The filtrate was mixed with water of equal volume, and recrystallized to obtain a pure tribromophenol product (38.1 g, purity by GC: 99.7%, bromine recovery rate 97.3%).

Example 7

An aqueous diquat dibromide solution (150.2 g, 40.5%) was mixed with hydrochloric acid (38.9 g, 36%), and dripped to a mixture of hydrogen peroxide (29.3 g, 46%), n-heptane (350.1 g), and bisphenol A (20.3 g). The temperature of the system was maintained at 60° C., and the dripping rate was controlled such that the dripping process was completed in about 40 min. The reaction solution was heated to 70-80° C., stirred fully, and reacted for 2 hrs. After the reaction was completed, the reaction solution was separated to obtain an aqueous phase and an organic phase after reaction. The aqueous phase was extracted with n-heptane (200 g), and separated to obtain an extracted aqueous phase and an extracted organic phase. The extracted aqueous phase was adjusted to pH 4.0 with ammonium bicarbonate (3.1 g), and concentrated by evaporating off a part of water to give 106.3 g of a mother liquor containing 42.0% diquat dichloride (cation content 30.3%). The yield was 99.0%.

The organic phase after reaction and the extracted organic phase were combined, concentrated, and crystallized to obtain a crude tetrabromobisphenol A product. The crude product was decolored by adding activated carbon, and purified by recrystallization in 95% ethanol to obtain a pure tetrabromobisphenol A product (46.8 g, purity by GC: 99.6%, bromine recovery rate 96.9%).

Example 8

An aqueous diquat dibromide solution (150.2 g, 40%) was mixed with hydrochloric acid (39.2 g, 36%), and dripped to a mixture of hydrogen peroxide (29.3 g, 46%), n-butanol (300.4 g), and bisphenol A (20.2 g). The temperature of the system was maintained at 60° C., and the dripping rate was controlled such that the dripping process was completed in about 40 min. The reaction solution was heated to 70-80° C., stirred fully, and reacted for 2 hrs. After the reaction was completed, the reaction solution was separated to obtain an aqueous phase and an organic phase after reaction. The aqueous phase was extracted with n-butanol (200 g), and separated to obtain an extracted aqueous phase and an extracted organic phase. The extracted aqueous phase was adjusted to pH 4.1 with aqueous ammonia (3.5 g, 25%), and concentrated by evaporating off a part of water to give 107.8 g of a mother liquor containing 41.7% diquat dichloride (cation content 30.1%). The yield was 99.7%.

The organic phase after reaction and the extracted organic phase were combined, concentrated, and crystallized to obtain a crude tetrabromobisphenol A product. The crude product was decolored by adding activated carbon, and purified by recrystallization in 95% ethanol to obtain a pure tetrabromobisphenol A product (45.8 g, purity by GC: 99.5%, bromine recovery rate 95.9%).

Example 9

An aqueous diquat dibromide solution (150.2 g, 40%) was mixed with hydrochloric acid (39.0 g, 36%), and dripped to a mixture of hydrogen peroxide (29.3 g, 46%), n-butanol (200.4 g), and p-cyanophenol (20.8 g). The temperature of the system was maintained at 60° C., and the dripping rate was controlled such that the dripping process was completed in about 40 min. The reaction solution was heated to 70-80° C., stirred fully, and reacted for 1 hr. After the reaction was completed, the reaction solution was cooled to 10° C. and filtered. The solid was a crude product of 2,6-dibromo-4-cyanophenol. The filtrate was separated to obtain an aqueous phase and an organic phase. The aqueous phase was adjusted to pH 3.5 with ammonium bicarbonate (3.0 g), and concentrated by evaporating off a part of water to give 107.7 g of a mother liquor containing 41.7% diquat dichloride (cation content 30.1%). The yield was 99.6%.

The crude product of 2,6-dibromo-4-cyanophenol obtained after filtration was fully washed with 80% n-butanol, and dried to obtain a pure 2,6-dibromo-4-cyanophenol product (47.6 g, purity by GC: 99.7%, bromine recovery rate 98.1%).

What is claimed is:

1. A method for preparing 1,1'-ethylene-2,2'-bipyridinium dichloride, comprising: mixing an aqueous diquat dibromide solution with hydrochloric acid, dripping to a mixture of an organic solvent, a bromine absorbent, and an oxidant, and reacting at a temperature of 20-100° C. to produce 1,1'-ethylene-2,2'-bipyridinium dichloride, wherein the bromine absorbent is phenol, aniline, bisphenol A, bisphenol S, p-cyanophenol, 4-hydroxybiphenyl, ethyl propionate, toluene, thiophene, and p-hydroxybenzaldehyde, and wherein the oxidant is hydrogen peroxide.

2. The method for preparing 1,1'-ethylene-2,2'-bipyridinium dichloride according to claim 1, wherein after the reaction is completed, the reaction solution is cooled to 5-30° C., and a post-treatment is performed according to whether a solid is precipitated in the reaction solution, wherein if a solid is precipitated in the reaction solution, the reaction solution is filtered and separated to obtain an aqueous phase and an organic phase after reaction, the aqueous phase is adjusted to pH 3-7, and concentrated to obtain a mother liquor containing 1,1'-ethylene-2,2'-bipyridinium dichloride, wherein the solid is a crude bromide product, which is washed and dried to obtain a pure bromide product; and if no solid is precipitated in the reaction solution, the reaction solution is directly separated to obtain an aqueous phase and an organic phase after reaction; an organic solvent is added to the aqueous phase to further extract the remaining bromide in the aqueous phase, to obtain an extracted aqueous phase and an extracted organic phase; the extracted aqueous phase is adjusted to pH 3-7, and concentrated to obtain a mother liquor containing 1,1'-ethylene-2,2'-bipyridinium dichloride; and the organic phase after reaction and the extracted organic phase are combined, concentrated, and crystallized to obtain a crude bromide product, which is then post-treated to obtain a pure bromide product.

3. The method for preparing 1,1'-ethylene-2,2'-bipyridinium dichloride according to claim 2, wherein the cation content in the mother liquor containing 1,1'-ethylene-2,2'-bipyridinium dichloride is 20-30%.

4. The method for preparing 1,1'-ethylene-2,2'-bipyridinium dichloride according to claim 1, wherein the molar ratio of 1,1'-ethylene-2,2'-bipyridinium dibromide to hydrochloric acid is 1:2-2.5;

the molar ratio of 1,1'-ethylene-2,2'-bipyridinium dibromide to the oxidant is 1:2-3; and the molar amount of the bromine absorbent is 1-1.2 times the theoretical molar amount of the bromine absorbent.

5. The method for preparing 1,1'-ethylene-2,2'-bipyridinium dichloride according to claim 1, wherein the content in percentage by weight of hydrochloric acid is 30-36%; and the content in percentage by weight of hydrogen peroxide is 20-50%.

6. The method for preparing 1,1'-ethylene-2,2'-bipyridinium dichloride according to claim 1, wherein the organic solvent in the reaction system is benzene, chlorobenzene, dichloroethane, dibromoethane, cyclohexane, n-heptane, and a $C_3$-$C_7$ monohydric alcohol.

7. The method for preparing 1,1'-ethylene-2,2'-bipyridinium dichloride according to claim 1, wherein the reaction temperature during the dripping process is controlled at 20-60° C., and the dripping rate based on diquat dibromide is 1.5-3.0 g/min; after the dripping is completed, the temperature is raised to 70-100° C. and the reaction is continued for 1-2 hrs.

8. The method for preparing 1,1'-ethylene-2,2'-bipyridinium dichloride according to claim 1, wherein the reaction temperature is 50-100° C.

9. The method for preparing 1,1'-ethylene-2,2'-bipyridinium dichloride according to claim 8, wherein the reaction temperature during the dripping process is controlled at 50-60° C., and the dripping rate based on diquat dibromide is 1.5-3.0 g/min; after the dripping is completed, the temperature is raised to 70-100° C. and the reaction is continued for 1-2 hrs.

* * * * *